United States Patent [19]

Marinkovich

[11] Patent Number: 4,697,587
[45] Date of Patent: Oct. 6, 1987

[54] DISPOSABLE MOUTH-TO-MOUTH RESUSCITATION DEVICE

[76] Inventor: Vincent S. Marinkovich, 939 S. Cabrillo Ave., #4, San Pedro, Calif. 90731

[21] Appl. No.: 846,808

[22] Filed: Apr. 1, 1986

[51] Int. Cl.⁴ .......................................... A61M 16/00
[52] U.S. Cl. ........................... 128/203.11; 128/207.16
[58] Field of Search ..................... 128/202.28, 203.11, 128/207.16, 912

[56] References Cited

U.S. PATENT DOCUMENTS 4,520,811  6/1985  White et al. ................... 128/203.11
4,535,765  8/1985  Paoluccio et al. ............. 128/203.11

FOREIGN PATENT DOCUMENTS 1150875  5/1969  United Kingdom ............... 128/912

*Primary Examiner*—Henry J. Recla
*Attorney, Agent, or Firm*—Fulwider, Patton, Rieber, Lee & Utecht

[57] ABSTRACT

A disposable mouth-to-mouth resuscitation device which avoids mouth-to-mouth contact of a rescuer with the victim being resuscitated, and which prevents exhaled vomit from the victim from coming into contact with the rescuer. The device includes a body having a mouthpiece into which the rescuer breathes. The mouthpiece includes a mask that covers the mouth of the victim during resuscitation. A tongue depressor tube insertable into a victim's mouth is releasably attached to the body. A flapper valve disposed in the body permits the victim to exhale breath and vomit from coming into contact with the mouth of the rescuer. The victim's breath exits through an escape port that bypasses the flapper valve.

7 Claims, 5 Drawing Figures

DISPOSABLE MOUTH-TO-MOUTH RESUSCITATION DEVICE

BACKGROUND OF THE INVENTION

During mouth-to-mouth resuscitation it is important to prevent mouth-to-mouth contact between the rescuer and the victim, and also to prevent vomit expelled from the victim from contacting the rescuer. If such contact occurs it is possible to transmit serious communicable diseases from the victim to the rescuer, e.g. Herpes, Aids or tuberculosis. Mechanical resuscitation devices solve this problem but are very expensive, and also difficult to carry to off-the-road sites.

Non-mechanical mouth-to-mouth resuscitation devices have been heretofore proposed. Such non-mechanical mouth-to-mouth resuscitation devices, however, must generally be sterilized after each use because the cost of such devices does not permit them to be discarded after each use. A non-mechanical mouth-to-mouth resuscitation device which is claimed to be disposable is disclosed in U.S. Pat. No. 3,957,046 issued May 18, 1976. Such device, however, is of comparatively large dimensions and its cost is therefore of such a magnitude as to discourage it from being discarded after each use. Moreover, such device utilizes a tube of a fixed length that is inserted into the victim's mouth, even though the device must be employed with various sizes of adults as well as children. It is desirable that a comparatively long tube be used with a large person, and that a shorter tube be utilized with a small person or child.

SUMMARY OF THE INVENTION

It is a major object of the present invention to provide a non-mechanical mouth-to-mouth resuscitation device that is simple in design and which may be fabricated from inexpensive parts whereby such device may be used only once and thereafter discarded.

Another object of the present invention is to provide a mouth-to-mouth resuscitation device which incorporates readily interchangeable tubes of varying lengths to be inserted into a victim's mouth depending upon the size of such victim.

A further object of the present invention is to provide a mouth-to-mouth resuscitation device which is simple to operate in emergency conditions even by inexperienced recuers.

An additional object of the present invention is to provide a mouth-to-mouth resuscitation device which permits the victim to exhale breath, but which prevents vomit emitted by the victim from coming into contact with the rescuer to thereby inhibit the transfer of communicable diseases from the victim to the rescuer.

These and other objects and advantages of the present invention will become apparent from the following detailed description, when taken in conjunction with the attached drawings.

DESCRIPTION OF A PREFERRED EMBODIMENT

Figure 1:
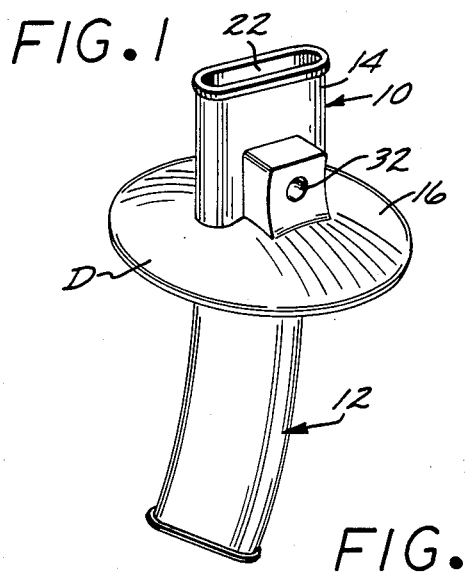
FIG. 1 is a perspective view of a disposable mouth-to-mouth resuscitation device embodying the present invention.
Figure 2:
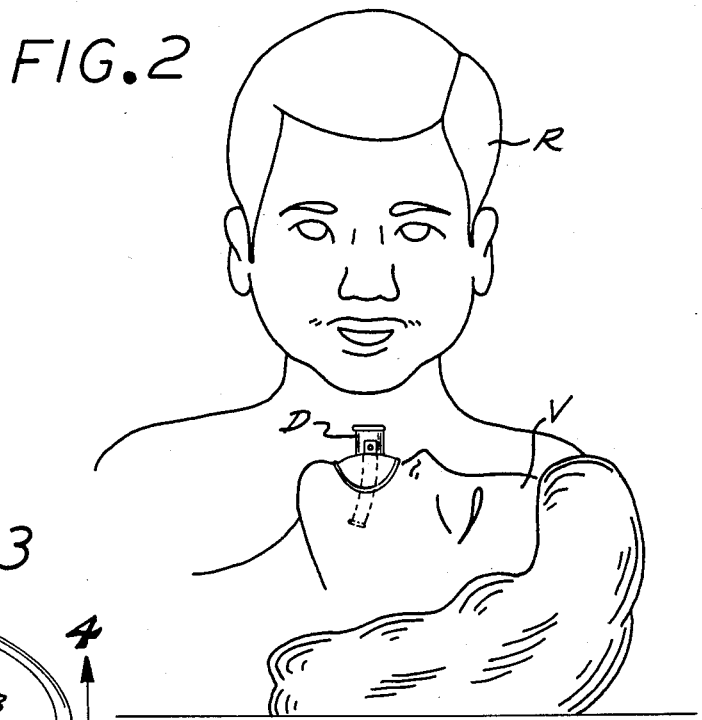
FIG. 2 is a perspective view of a victim about to be resuscitated by a rescuer utilizing said device.

Referring to the drawings, there is shown a preferred form of disposable mouth-to-mouth resuscitation device D embodying the present invention. Such device includes a hollow body, generally designated 10, from which depends 2 tongue depressor tube, generally designated 12, adapted to be inserted into the mouth of a victim V being resuscitated, as indicated in FIG. 2. The body 10 includes an upwardly extending mouthpiece 14 that is engaged by the mouth of a rescuer R. A mask 16 formed on the lower portion of the body engages and covers the mouth of the victim V. The body 10 also incorporates a flapper-type check valve 20 that permits the victim to exhale breath, but which automatically closes under the pressure of vomit emitted by the victim so as to prevent contact of the vomit with the rescuer R.

More particularly, the body 10 is preferably of integral construction and will be molded from a suitable rigid, or semi-rigid, synthetic plastic. Mouthpiece 14 is formed with an elongated in cross-section air-transfer passage 22 which terminates at its lower end in a valve seat 24 that receives flapper check valve 21.

Valve seat 24 defines the upper surface of a valve chamber 25. The check valve 20 is generally flat and formed of a suitable flexible material, such as a natural or synthetic rubber or plastic. One side of the flapper valve is affixed to the body 14 by a rivet 23. An escape passage 32 formed in body 14 extends upwardly from valve chamber 25 through a shoulder 36 that projects integrally from one side of mouthpiece 14. The sides of valve chamber 25 are defined by a socket 37 that integrally depends from body 10.

Mask 16 is of a generally semi-hemispherical configuration and its dimensions are adequate to cover the mouth of a victim V without contacting the victim's nose.

Figure 3:
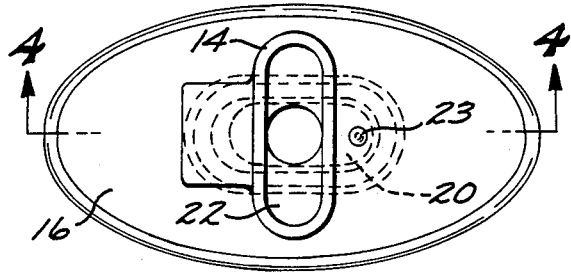
FIG. 3 is a top plan view of said device.
Figure 4:
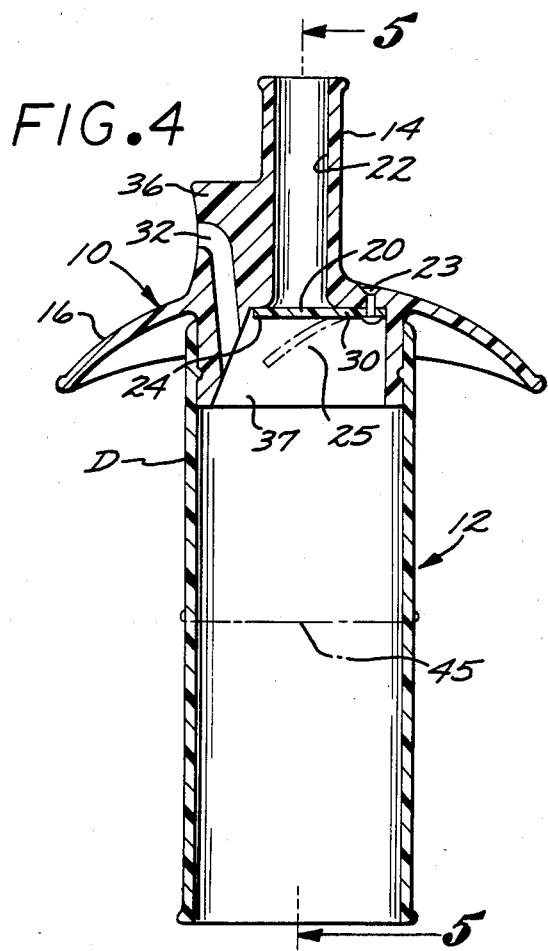
FIG. 4 is a vertical sectional view taken along 4—4 of FIG. 3.
Figure 5:
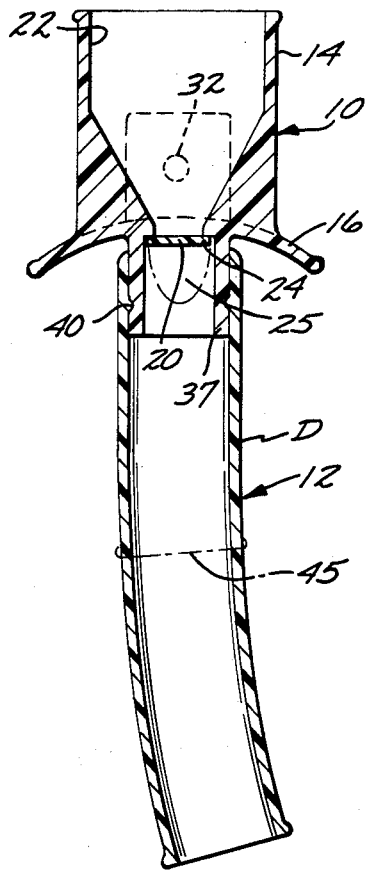
FIG. 5 is a vertical sectional view taken along line 5—5 of FIG. 4.

The tongue depressor tube 12 is preferably molded from a synthetic plastic material that is sufficiently flexible to permit the tube to follow the contours of a victim's mouth and throat. Such tube 12 is removably secured to the socket member 37 of the body 10, as by means of a conventional snap-together, quick-release tongue and groove joint 40 that releasably interconnects the lower end of body socket 37 and the upper end of the tube. It will be understood, however, that other types of quick-release connection means may be utilized. Referring to FIGS. 3, 4 and 5, it should be understood that various lengths of tongue depressor tubes 12 may be employed with a single body 10. Thus, the longest tube 12 (shown in solid outline) would be utilized when the victim is of normal physical proportions. A shorter tube, the bottom of which is designated by dotted line 45, would be employed with a victim of lesser physical size, such as a child, or a small woman. Preferably, the tongue depressor tube 12 will be of curved configuration to permit the lower portion thereof to rest on the vicim's tongue to prevent such victim from swallowing his tongue. The mouthpiece 14 is generally perpendicular to the tougue depressor tube 12, as shown clearly in FIG. 3.

In the use of the aforedescribed device, the rescuer R will position his body at approximately right angles to the body of the victim V. After the tongue depressor tube 12 of the desired length has been positioned upon body socket 37 the tube is inserted within the mouth of the victim, as indicated in FIG. 2. It will be understood that the mask 16 prevents contact between the mouths of the victim and the rescuer and hence restraining the vicim's saliva from entering the rescuer's mouth, to thereby inhibit the transmission of communicable diseases from the victim to the rescuer. The rescuer R then breathes into the mouthpiece 14 with one of his thumbs and fingers closing off the victim's nostrils in accordance with normal resuscitation procedures. The rescuer will use another of his fingers to cover the upper end of escape passage 32. The flapper valve 20 flexes downwardly as the rescuer breathes into the mouthpiece. After each breath, the rescuer will raise his lips from the mouthpiece. When the victim exhales, the flapper valve 20 will rise into sealing engagement with valve set 24 within its valve chamber 25 whereby the victim's breath does not contact the rescuer's mouth. Instead breath exhaled by the victim will pass out of the body 10 through escape passage 32. Should the victim vomit, the emitted vomit will be prevented from contacting the mouth of rescuer by seating of the flapper valve. In this manner the transmission of communicable diseases by contact of the victim's vomit with the rescuer is inhibited. When the victim vomits, the resuscitation device D is withdrawn from his mouth.

From the foregoing description, it will be apparent that a device constructed in accordance with the present invention may be inexpensive to manufacture, and is extremely simple to operate, even under emergency conditions by inexperienced rescuers.

Various modifications and changes may be made with respect to the foregoing detailed description without departing from the spirit of the present invention.

I claim:

1. A mouth-to-mouth resuscitation device for use by a rescuer with a victim, such device comprising:
    a generally vertically extending hollow body formed at its lower end with a depending socket;
    an upwardly extending mouthpiece formed on said body that terminates at its lower end in a valve seat;
    a vertical air-transfer passage extending through said mouthpiece in alignment with said valve seat;
    a mask on said body below said mouthpiece to cover the mouth of the victim;
    a valve chamber formed in said body socket, said valve seat defining the upper surface of said valve chamber;
    a downwardly opening flapper valve disposed in said valve chamber that is normally biased upwardly into sealing engagement with said valve seat, but which flexes downwardly when the rescuer breathes into said mouthpiece;
    a tongue depressor tube secured to and depending from said socket body for insertion into the mouth of the victim;
    an escape passage extending upwardly through said body from said valve chamber to one side of said body, with the upper end of said escape passage being covered by a finger of the rescuer when the rescuer breaths into said mouthpiece; and
    with breath and vomit expelled from the victim passing through said escape passage, and with said flapper valve restraining breath and vomit of the victim from contacting the mouth of the rescuer.

2. A mouth-to-mouth resuscitation device as set forth in claim 1 wherein said mouthpiece and said tongue depressor tube are elongated in cross-section with their passages perpendicular to one another.

3. A mouth-to-mouth resuscitation device as set forth in claim 1 wherein a quick-release connection is interposed between said body and said insertion tube whereby a plurality of insertion tubes of varying lengths may be utilized with a single body.

4. A mouth-to-mouth resuscitation device as set forth in claim 1 wherein a quick-release connection is interposed between said body socket and said insertion tube whereby a plurality of insertion tubes of varying lengths may be utilized with a single body.

5. A mouth-to-mouth resuscitation device as set forth in claim 4 wherein the quick-release connection is a snap-together tongue and groove joint.

6. A mouth-to-mouth resuscitation device as set forth in claim 5 wherein said insertion tube is curved and flexible to readily conform to the configuration of the victim's mouth and throat.

7. A mouth-to-mouth resuscitation device as set forth in claim 4 wherein said insertion tube is curved and flexible to readily conform to the configuration of the victim's mouth and throat.

* * * * *